US007501240B2

(12) United States Patent
Birkner et al.

(10) Patent No.: US 7,501,240 B2
(45) Date of Patent: Mar. 10, 2009

(54) METHOD FOR BISULFITE TREATMENT

(75) Inventors: Christian Birkner, Uffing (DE); Christine Markert-Hahn, Penzberg (DE); Herbert von der Eltz, Weilheim (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 10/573,215

(22) PCT Filed: Dec. 1, 2004

(86) PCT No.: PCT/EP2004/013627

§ 371 (c)(1), (2), (4) Date: Sep. 19, 2006

(87) PCT Pub. No.: WO2005/054502

PCT Pub. Date: Jun. 16, 2005

(65) Prior Publication Data

US 2007/0190530 A1 Aug. 16, 2007

(30) Foreign Application Priority Data

Dec. 2, 2003 (EP) .................................. 03027754

(51) Int. Cl.
*C12Q 1/68* (2006.01)
*C07H 21/04* (2006.01)

(52) U.S. Cl. .......................................... 435/6; 536/23.1
(58) Field of Classification Search .................. 435/6; 536/23.1
See application file for complete search history.

(56) References Cited

U.S. PATENT DOCUMENTS

| 4,683,202 A | 7/1987 | Mullis et al. .................... 435/91 |
| 5,130,238 A | 7/1992 | Malek et al. ..................... 435/91 |
| 5,137,806 A | 8/1992 | LeMaistre et al. ................ 435/6 |
| 5,210,015 A | 5/1993 | Gelfand et al. .................. 435/6 |
| 5,234,809 A | 8/1993 | Boom et al. ..................... 435/91 |
| 5,487,972 A | 1/1996 | Gelfand et al. .................. 435/6 |
| 5,552,277 A | 9/1996 | Nelson et al. .................... 435/6 |
| 5,595,890 A | 1/1997 | Newton et al. ............... 435/91.2 |
| 5,639,611 A | 6/1997 | Wallace et al. .................. 435/6 |
| 5,786,146 A | 7/1998 | Herman et al. ................... 435/6 |
| 5,804,375 A | 9/1998 | Gelfand et al. .................. 435/6 |
| 6,174,670 B1 | 1/2001 | Wittwer et al. .................. 435/6 |
| 6,331,393 B1 | 12/2001 | Laird et al. ..................... 435/6 |
| 2005/0095623 A1* | 5/2005 | Zon et al. ....................... 435/6 |

FOREIGN PATENT DOCUMENTS

| EP | 0 200 362 B1 | 12/1986 |
| EP | 0 201 184 A2 | 12/1986 |
| EP | 0 389 063 A2 | 9/1990 |
| EP | 0 439 182 A2 | 7/1991 |
| EP | 1 394 172 A1 | 3/2004 |
| EP | 1 443 052 A1 | 8/2004 |
| WO | WO 90/01069 | 2/1990 |
| WO | WO 90/06045 | 6/1990 |
| WO | WO 92/02638 | 2/1992 |
| WO | WO 96/41811 | 12/1996 |
| WO | WO 99/16781 | 4/1999 |
| WO | WO 99/40098 | 8/1999 |
| WO | WO 00/32762 | 6/2000 |
| WO | WO 00/37291 | 6/2000 |
| WO | WO 01/37291 A1 | 5/2001 |
| WO | WO 01/98528 A2 | 12/2001 |
| WO | WO 02/31186 A2 | 4/2002 |
| WO | WO 2005/054502 A1 | 6/2005 |

OTHER PUBLICATIONS

PCT/EP2004/013627, Mar. 2, 2005.
Abramson, R., et al., 1993, "Nucleic acid amplification technologies", *Current Opinion in Biotechnology*, 4:41-47.
Alderton, R., et al., 1992, "Magnetic Bead Purification of M13 DNA Sequencing Templates", *Analytical Biochemistry*, 201:166-169.
Ausubel F., et al., 2001, "Current Protocols In Molecular Biology", *John Wiley & Sons, Inc.*, Supplement 55-56:1-10.
Barany, F., 1991, "The Ligase chain Reaction in a PCR World", *PCR Methods and Applications*, 5-16.
Barany, F., 1991, "Genetic disease detection and DNA amplification using cloned thermostable ligase", *Proc. Natl. Acad. Sci. USA*, 88:189-193.
Benyajati, C., et al., "Alcohol dehydrogenase in Drosophila: isolation and characterization of messenger RNA and eDNA clone", *Nucleic Acids Research*, 8:5649-5667.
Clark, S., et al., 1994, "High sensitivity mapping of methylated cytosines", *Nucleic Acids Research*, 22(15):2990-2997.
Feil, R., et al., 1994, "Methylation analysis on individual chromosomes: improved protocol for bisulphate genomic sequencing", *Oxford University Press*, 22(4):695-696.
Frommer, M., 1992, "A genomic sequencing protocol that yields a positive display of 5-methylcytosine residues in individual DNA strands", *Proc. Natl. Acad. Sci. USA*, 89:1827-1831.
Grigg, G., et al., 1994, "Sequencing 5-Methylcytosine Residues in Genomic DNA", *BioEssays*, 16(6):431436.
Grigg, G., 1996, "Sequencing 5-methylcytosine residues by the bisulphate method", *The Journal of Seq.&Mapping* 6:189-198.
Grunau, C., et al., 2001, "Bisulfite genomic sequencing: systematic investigation of critical experimental parameters", *Nucleic Acids Research*, 29(13e65):1-7.
Guatelli, J., et al., 1990, "Isothermal, in vitro amplification of nucleic acids by a multienzyme reaction modeled after retroviral replication", *Proc. Natl. Acad. Sci. USA*, 87:1874-1878.

(Continued)

*Primary Examiner*—Suryaprabha Chunduru
(74) *Attorney, Agent, or Firm*—Olga Kay; Charles M. Doyle

(57) ABSTRACT

The invention is related to the detection of a methylated cytosine in a nucleic acid wherein guanidinium hydrogen sulfite is used for the preparation of a solution containing guanidinium ions and sulfite ions and subsequent modification of the nucleic acid. Thereby, a non-methylated cytosine is converted to uracil. The invention further discloses kits for performing the methods of the invention.

8 Claims, 4 Drawing Sheets

OTHER PUBLICATIONS

Jakobi R., et al., 1988, "Filter-Supported Preparation of λ Phage DNA", *Analytical Biochemistry*, 175:196-201.

Komlyama, M., et al., 1994, "Catalysis of Diethylenetriamine for Bisulfite-Induced Deamination of Cytosine in Oligodeoxyribonucleotides", *Tetrahedron Letters*, 35(44):8185-8188.

Kwoh, D., et al., 1989, "Transcription-based amplification system and detection of amplified human immunodeficiency virus type 1 with a bead-based sandwich hybridization format", *Proc. Natl. Acad. Sci. USA*, 86:1173-1177.

Marko, M., et al., 1982, "A Procedure for the Large-Scale Isolation of Highly Purified Plasmid DNA Using Alkaline Extraction and Binding to Glass Powder", *Analytical Biochemistry*, 121:382-387.

Morrow, C., et al., 1989, "Structure of Human Genomic Gluthathione S-transferase-Λ gene", *Gene*, 75:3-11.

Oakeley, E., 1999, "DNA methylation analysis: a review of current methodologies", *Pharmacology & Therapeutics*, 84:389-400.

Olek, A., et al., 1996, "A modified and improved method for bisulphate based cytosine methylation analysis", *Nucleic Acids Research*, 24(24):5064-5066.

Paulin, R., et al., 1998, "Urea improves efficiency of bisulphate-mediated sequencing of 5'-methylcytosine in genomic DNA", *Nucleic Acids Research*, 26(21):5009-5010.

Raizis, A., et al., 1995, "A Bisulfite method of 5-Methylcytosine Mapping That Minimizes Template Degradation", *Analytical Biochemistry*, 226:161-166.

Vogelstein, B., et al., 1978, "Preparative and analytical purification of DNA from agarose", *Proc. Natl. Acad. Sci. USA*, 76(2):615-619.

Warnecke, P., et al., 2002, "Identification and resolution of artifacts in bisulfite sequencing", *Methods*, 27:101-107.

Whelen, A., et al., 1996, "The Role of Nucleic Acid Amplification and Detection in the Clinical Microbiology Laboratory", *Annu. Rev. Microbiol*, 50:349-379.

Wu, D., et al., 1989, The Ligation Amplification Reaction (LAR)—Amplification of Specific DNA Sequences Using Sequential Rounds of Template-Dependent Ligation.

* cited by examiner

METHOD FOR BISULFITE TREATMENT

BACKGROUND OF THE INVENTION

1. Field Of Invention

The invention is related to the detection of a methylated cytosine in a nucleic acid wherein guanidinium hydrogen sulfite is used for the preparation of a solution containing guanidinium ions and sulfite ions and subsequent modification of the nucleic acid. Thereby, a non-methylated cytosine is converted to uracil. The invention further discloses for performing the methods of the invention.

2. Description Of The Related Art

Genes constitute only a small proportion of the total mammalian genome, and the precise control of their expression in the presence of an overwhelming background of noncoding desoxyribonucleic acid (DNA) presents a substantial problem for their regulation. Noncoding DNA, containing introns, repetitive elements, and potentially active transposable elements requires effective mechanisms for its long term silencing. Mammals appear to have taken advantage of the possibilities afforded by cytosine methylation to provide a heritable mechanism for altering DNA-protein interactions to assist in such silencing. DNA methylation is essential for the development of mammals; and plays a potential role during aging and cancer. The involvement of methylation in the regulation of gene expression and as an epigenetic modification marking imprinted genes is well established. In mammals, methylation occurs only at cytosine residues and more specifically only on cytosine residues adjacent to a guanosine residue, i.e. at the sequence CG. The detection and mapping of DNA methylation sites are essential steps towards understanding the molecular signals which indicate whether a given sequence is methylated.

This is currently accomplished by the so-called bisulfite method described by Frommer, M., et al., Proc. Natl. Acad. Sci. USA 89 (1992) 1827-1831) for the detection of 5-methyl-cytosines. The bisulfite method of mapping 5-methylcytosine uses the effect that sodium hydrogen sulfite reacts with cytosine but not or only poorly with 5-methyl-cytosine. Cytosine reacts with bisulfite to form a sulfonated cytosine reaction intermediate being prone to deamination resulting in a sulfonated uracil which can be desulfonated to uracil under alkaline conditions. It is common knowledge that uracil has the base pairing behavior of thymine different to the educt cytosine whereas 5-methylcytosine has the base pairing behavior of cytosine. This makes the discrimination of methylated or non-methylated cytosines possible by e.g. bisulfite genomic sequencing (Grigg, G., and Clark, S., Bioessays 16 (1994) 431-436; Grigg, G. W., DNA Seq. 6 (1996) 189-198) or methylation specific PCR (MSP) disclosed in U.S. Pat. No. 5,786,146.

There are various documents addressing specific aspects of the bisulfite reaction (Benyajati, C., et al., Nucleic Acids Res. 8 (1980) 5649-5667) make general investigations to the bisulfite modification of 5-methyl-deoxycytosine and deoxycytosine (Olek, A., et al., Nucleic Acids Res. 24 (1996) 5064-5066) disclose a method for bisulfite base sequencing whereby bisulfite treatment and subsequent PCR steps are performed on material embedded in agarose beads. In the bisulfite method as disclosed by Clark, S. J., et al., Nucleic Acids Res. 22 (1994) 2990-2997, the sample is desalted after deamination.

Raizis, A. M., et al., Anal. Biochem. 226 (1995) 161-166 disclose a bisulfite method of 5-methylcytosine mapping that minimizes template degradation. They investigate the influence of pH, temperature and time of reaction. Similar investigations have been made by Grunau, C., et al., Nucleic Acids Res. 29 (2001) E65-5 or Warnecke, P. M., et al., Methods 27 (2002) 101-107. Different additional components in the bisulfite mixture are disclosed by WO 01/98528 or by Paulin, R., et al., Nucleic Acids Res. 26 (1998) 5009-5010. An additional bisulfite step after bisulfite treatment and PCR is disclosed in WO 02/31186. Komiyama, M., and Oshima, S., Tetrahedron Letters 35 (1994) 8185-8188) investigate the catalysis of bisulfite-induced deamination of cytosine in oligodeoxyribonucleotides.

Kits for performing bisulfite treatments are commercially available from Intergen, distributed by Serologicals Corporation, Norcross, Ga., USA, e.g. CpGenome™ DNA modification kit.

A variation of the bisulfite genomic sequencing method is disclosed by Feil, R., et al., Nucleic Acids Res. 22 (1994) 695-696, whereby the genomic DNA is bound to glass beads after deamination and washed. After elution the nucleic acid is desulfonated. It is known that nucleic acids can be isolated by the use of their binding behavior to glass surfaces, e.g. adsorption to silica gel or diatomic earths, adsorption to magnetic glass particles (MGPs) or organo silane particles under chaotropic conditions. Extraction using solid phases usually contains the steps of adding the solution with the nucleic acids to the solid phase under conditions allowing binding of the substance of interest to the solid phase, removal of the remainder of the solution from the solid phase bound nucleic acids and subsequent release of the nucleic acids from the solid phase into a liquid eluate (sometimes called elution). The result of the such process is usually a solution containing the substance of interest in dissolved state.

Guanidinium hydrogen sulfite is known from various documents. U.S. Pat. No. 2,437,965 discloses a method for relaxing keratinous fibers using guanidinium hydrogen sulfite. U.S. Pat. No. 2,654,678 discloses the antistatic treatment of shaped articles using guanidinium salts. U.S. Pat. No. 4,246,285 discloses skin conditioning compositions containing guanidine inorganic salts. DE19527313 discloses guanidine derivatives and cosmetic articles containing them.

All prior art methods for the bisulfite treatment have disadvantages. Therefore, the problem to be solved by the present invention was to provide a method wherein guanidinium hydrogen sulfite is used.

SUMMARY OF THE INVENTION

The invention is related to a method for the conversion of a cytosine base in a nucleic acid to an uracil base comprising the steps of a) providing a solution that contains a nucleic acid,
b) providing guanidinium hydrogen sulfite and preparing a solution comprising guanidinium and sulfite ions,
c) mixing the solutions from step a) and b)
d) incubating the solution obtained in step c) containing the nucleic acid and guanidinium and sulfite ions whereby the nucleic acid is deaminated,
e) incubating the deaminated nucleic acid under alkaline conditions whereby the deaminated nucleic acid is desulfonated,
f) isolating the deaminated nucleic acid.

In a further embodiment of the invention, guanidinium hydrogen sulfite is used for chemically modifying a nucleic acid, particularly in a method wherein a cytosine base in a nucleic acid is converted to an uracil base. In another embodiment of the invention, guanidinium hydrogen sulfite is used to prepare a solution comprising guanidinium and sulfite ions, particularly the solution is used for converting a cytosine base in a nucleic acid to an uracil base.

In another embodiment of the invention, a kit containing guanidinium hydrogen sulfite is provided and uses of the kit according to the invention for a reaction wherein a cytosine base in a nucleic acid is converted to an uracil base in the presence of bisulfite ions.

According to the invention the term a "bisulfite reaction", "bisulfite treatment" or "bisulfite method" shall mean a reaction for the conversion of a cytosine base, in particular cytosine bases, in a nucleic acid to an uracil base, or bases, preferably in the presence of bisulfite ions whereby preferably 5-methyl-cytosine bases are not significantly converted. This reaction for the detection of methylated cytosines is described in detail by Frommer et al., supra and Grigg and Clark, supra. The bisulfite reaction contains a deamination step and a desulfonation step which can be conducted separately or simultaneously (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra).

DESCRIPTION OF THE FIGURES

FIGS. 2 to 4 show HPLC profiles of the reaction mixtures after incubation for certain time periods and in the presence of different disseminating reagents as indicated in section 2.1.2 et seq.

FIG. 2a) 1 M sodium hydrogensulfite, 30 min;
FIG. 2b) 1 M guanidinium hydrogensulfite, 30 min;
FIG. 3b) 2 M guanidinium hydrogensulfite, 30 min.

DETAILED DESCRIPTION OF THE INVENTION

Figure 1:
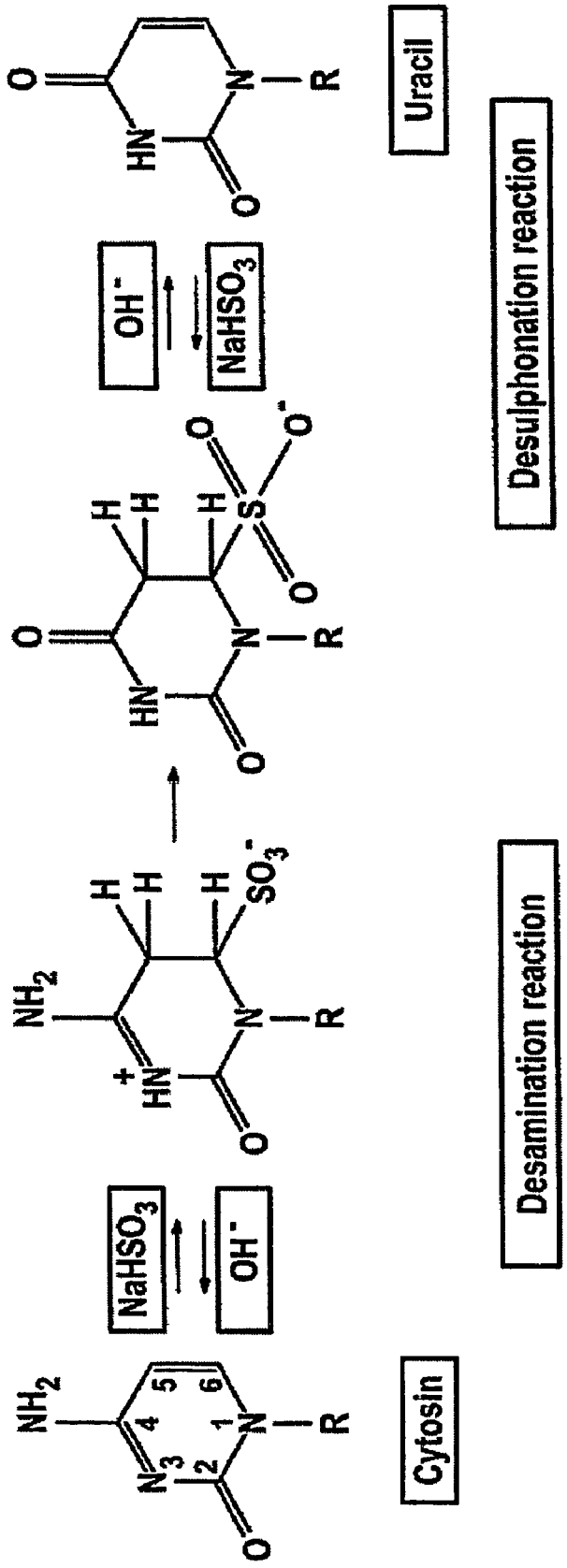
FIG. 1 shows the reaction of cytosine with bisulfite. The steps of the bisulfite method

The invention is related to a method for the conversion of a cytosine base in a nucleic acid to an uracil base comprising the steps of
a) providing a solution, preferably a sample, that contains a nucleic acid,
b) providing guanidinium hydrogen sulfite and preparing a solution comprising guanidinum and sulfite ions,
c) mixing the solutions from step a) and b) or preferably the sample from step a) and the solution from step b),
d) incubating the solution obtained in step c) containing the nucleic acid and guanidinium and sulfite ions whereby the nucleic acid is deaminated,
e) incubating the deaminated nucleic acid under alkaline conditions whereby the deaminated nucleic acid is desulfonated,
f) isolating the deaminated nucleic acid.

Guanidinium hydrogen sulfite is a salt and used in solid form, i.e. it should be primarily in dry form and not contain water although minor amounts of water, including crystal water may be present. Guanidinium hydrogen sulfite may be produced as described in the invention (see Example 1) or as described in U.S. Pat. Nos. 2,437,965, 2,654,678, 4,246,285 or DE 19527313.

The preparation of the solution comprising guanidinium and sulfite ions is accomplished by methods known to the expert skilled in the art, particularly by combining water or a buffered solution and the guanidinium hydrogen sulfite and mechanically agitation by e.g. shaking, stirring, pipetting the solution up and down or any other suitable means known to the expert skilled in the art. As said above, the guanidinium hydrogen sulfite may also be dissolved in a buffered solution which may be an aequeous buffer, may contain further substances as organic substances, salts and buffering constituents known to the expert in the field as phosphate, Tris, HEPES or other suitable buffers.

The expert skilled in the art knows how to perform the bisulfite reaction, e.g. by referring to Frommer et al., supra or Grigg and Clark, supra who disclose the principal parameters of the bisulfite reaction. From Grunau et al., supra, it is known to the expert in the field what variations of the bisulfite method are possible. The influence of incubation time and temperature on deamination efficiency and parameters affecting DNA degradation is disclosed. In summary, in the deamination step a buffer containing bisulfite ions and chaotropic agents and optionally further reagents as an alcohol or stabilizers as hydroquinone are employed and the pH is in the acidic range. The concentration of bisulfite is between 0.1 to 6 M bisulfite, preferably 1 M to 5.5 M, the concentration of the chaotropic agent is between 1 to 8 M, whereby in general preferably guanidinium salts are employed but guanidinium hydrogen sulfite according to the invention as described herein, the pH is in the acidic range, preferably between 4.5 to 6.5, the temperature is between 0° C. to 90° C., preferably between room temperature (25° C.) to 90° C., and the reaction time is between 30 min to 24 hours or 48 hours or even longer, but preferably between 1 hour to 24 hours. The desulfonation step is performed by adding an alkaline solution or buffer as e.g. a solution only containing a hydroxide, e.g. sodium hydroxide, or a solution containing ethanol, sodium chloride and sodium hydroxide (e.g. 38% EtOH, 100 mM NaCl, 200 mM NaOH) and incubating at room temperature or elevated temperatures for several min, preferably 5 min to 60 min.

Therefore, in an embodiment of the invention, in the method according to the invention, the concentration of guanidinium ions and sulfite ions is 0.1 to 8 M, preferably 2 to 8 M. In an embodiment of the invention, the pH of the solutions in step b) and c) of the method according to the invention is in the acidic range, preferably between 4.5 to 6.5. In an embodiment of the method according to the invention, the incubation temperature in step d) and e) of the method according to the invention is between 0° C. to 90° C., preferably between 18° C. to 90° C. In an embodiment of the method according to the invention, the incubation time in step d) is between 30 min to 48 hours, preferably 24 hours. In an embodiment of the invention, the step e) in the method according to the invention is performed by adding an alkaline solution or buffer, preferably a solution containing a hydroxide, preferably sodium hydroxide, or a solution containing ethanol, sodium chloride and sodium hydroxide, preferably a solution containing 38% (volume/volume) ethanol, 100 mM NaCl, 200 mM NaOH. In an embodiment of the invention, in the method according to the invention, the incubation temperature in step e) is between 0° C. to 90° C., preferably between 18° C. to 90° C. The incubation time in step e) of the method according to the invention is between 5 min to 60 min. In another embodiment of the invention, the incubation parameters as described in EP03001854.3 may be used, wherein the nucleic acid is incubated in a solution for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid is deaminated.

Desalting of the nucleic acid can be performed using magnetic glass particles as described in WO96/41811 or desulfonation and/or desalting can be performed as described in EP 1 394 172.

In general, the method of the invention can be performed on solid surfaces as described in EP 1 394 172 or under the special conditions as described in EP 1 443 052.

In an embodiment of the invention, the nucleic acid is desoxyribonucleic acid (DNA), in particular genomic DNA or nucleic acid, i.e. the DNA or nucleic acid which is found in the organism's genome and is passed on to offspring as information necessary for survival. The phrase is used to distinguish between other types of DNA, such as found within plasmids. The source of the nucleic acid may be eukaryotic or prokaryotic, preferably from vertebrates, particularly from mammalians, most preferred from animals or humans.

The solution that contains a nucleic acid is preferably a sample that contains a nucleic acid. Other compounds may be present but it is preferred that the solution containing the nucleic acid is as pure as possible. In another embodiment, the solution contains other insoluble components, i.e. it is a suspension preferably containing material comprising glass as e.g. magnetic glass particles as described in EP 1 394 172. In an embodiment of the invention the solution or the sample containing the nucleic acid is obtained from a biological sample using e.g. solid phases (see e.g. WO96/41811 or WO01/37291 or the MagNAPure® System available from Roche Diagnostics, Mannheim Germany) or other methods known to the expert in the field (see e.g. Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY or commercial DNA isolation kits available e.g. from Qiagen, Hilden Germany). The biological sample comprises cells from multicellular organisms as e.g. human and animal cells such as Leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. The biological sample may be blood, blood plasma, blood serum or urine. The biological sample comprising the nucleic acid is lysed to create a mixture of biological compounds comprising nucleic acids and other components. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY. Then the nucleic acids are isolated from the lysis mixture using the methods and solid phases according to the invention and can then be subjected to the methods according to the invention, i.e. the bisulfite treatment according to the invention. Chaotropic agents are also used to lyse cells to prepare a mixture between nucleic acids and other biological substances (see e.g. Sambrook et al. (1989) or EP 0 389 063). Afterwards the material comprising glass or silica may be added and a purification effect results from the behavior of DNA or RNA to bind to material with a glass surface under these conditions i.e. in the presence of certain concentrations of a chaotropic agent, higher concentrations of organic solvents or under acidic conditions. Alternative methods may be used as well.

In another embodiment of the invention, a method is provided for the conversion of a cytosine base in a nucleic acid to an uracil base comprising the steps of a) providing guanidinium hydrogen sulfite and preparing a solution comprising guanidinum and sulfite ions, b) mixing the solution from step a) with a solution, preferably a sample, containing a nucleic acid, c) incubating the solution obtained in step b) containing the nucleic acid and guanidinium and sulfite ions whereby the nucleic acid is deaminated, d) incubating the deaminated nucleic acid under alkaline conditions whereby the deaminated nucleic acid is desulfonated, e) isolating the deaminated nucleic acid.

After the steps of the method according to the invention, further steps may be performed. In a preferred embodiment of the invention, the nucleic acid is amplified with the polymerase chain reaction (PCR; EP 0 201 184, EP-A-0 200 362, U.S. Pat. No. 4,683,202). The amplification method may also be the ligase Chain Reaction (LCR, Wu, D. Y., and Wallace, R. B., Genomics 4 (1989) 560-569 and Barany, F., Proc. Natl. Acad. Sci. USA 88 (1991) 189-193; Polymerase Ligase Chain Reaction (Barany, F., PCR Methods Appl. 1 (1991) 5-16); Gap-LCR(PCT Patent Publication No. WO 90/01069); Repair Chain Reaction (European Patent Publication No. EP 439,182 A2), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; PCT Patent Publication No. WO 92/0880A), and NASBA (U.S. Pat. No. 5,130, 238). Further, there are strand displacement amplification (SDA), transcription mediated amplification (TMA), and Qβ-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47). Particularly preferred amplification methods according to the invention are the methylation specific PCR method (MSP) disclosed in U.S. Pat. No. 5,786,146 which combines bisulfite treatment and allele-specific PCR (see e.g. U.S. Pat. Nos. 5,137,806, 5,595,890, 5,639,611). The bisulfite treatment may be performed according to the invention.

In a preferred embodiment, the method may further comprise the step of detecting the amplified nucleic acid. The amplified nucleic acid may be determined or detected by standard analytical methods known to the person skilled in the art and described e.g. in Sambrook, et al., Molecular Cloning, Cold Spring Harbor University Press (1989), Lottspeich and Zorbas, in "Bioanalytik" (1998), Eds. L. a. Zorbas, Spektrum Akademischer Verlag, Heidelberg, Berlin, Germany, or in Ausubel, F., et al., in "Current protocols in molecular biology" (1994), Eds. F. Ausubel, R. Brent and K. R. E., Wiley & Sons Verlag, N.Y. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridisation to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequences bind.

In a particularly preferred embodiment of the invention, the nucleic add is detected by measuring the intensity of fluorescence light during amplification. This method entails the monitoring of real time fluorescence. A particularly preferred method exploiting simultaneous amplification and detection by measuring the intensity of fluorescent light is the TaqMan® method disclosed in WO 92/02638 and the corresponding U.S. Pat. Nos. 5,210,015, 5,804,375, 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TaqMan® technology eliminates the need for a solid phase bound reaction complex to be formed and made detectable. In more general terms, the amplification and/or detection reaction of the method according to the invention is a homogeneous solution-phase assay. Further preferred method are the formats used in the LightCycler® instrument (see e.g. U.S. Pat. No. 6,174,670). Particularly preferred is the use of bisulfite treatment, amplification with or without methylation specific primers in the presence of a methylation-specific probe and real-time fluorescence detection as described in U.S. Pat. No. 6,331,393.

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time.

Preferably the method according to the invention is used in diagnostics, for diagnostic analysis or for bioanalytics, or for the screening of tissue or fluids from the human or even animal body for the presence of certain methylation pattern. Further, the method according to the invention is used to enhance the speed, accuracy or sensitivity of the detection of methylation sites in nucleic acids.

In an embodiment of the invention, guanidinium hydrogen sulfite is used for chemically modifying a nucleic acid, preferably wherein a cytosine base in a nucleic acid is converted to an uracil base. In another embodiment of the invention, guanidinium hydrogen sulfite is used to prepare a solution comprising guanidinum and sulfite ions. Preferably, the solution is used for converting a cytosine base in a nucleic acid to an uracil base.

In another preferred embodiment, the present invention is directed to a kit for performing a bisulfite reaction containing guanidinium hydrogen sulfite or a solution comprising bisulfite ions and guanidinium prepared from guanidinium hydrogen sulfite. Generally, kits known in the art further comprise plastics ware which may be used during the bisulfite procedure as e.g. microtiter-plates in the 96 or 384 well format or reaction tubes manufactured e.g. by Eppendorf, Hamburg, Germany. Further, additional reagents may be present which contain buffers suitable for use in the present invention, primers, probes, a DNA polymerase, preferably a thermostabile DNA polymerase and possibly nucleotides. Therefore, in an embodiment of the invention a kit is provided comprising guanidinium hydrogen sulfite, primers, probes, a DNA polymerase and nucleotides. Preferably, the kit according to the invention is used for a reaction wherein a cytosine base, preferably cytosine bases, in a nucleic acid is converted to an uracil base, preferably uracil bases, in the presence of bisulfite ions whereby preferably 5-methyl-cytosine bases are not significantly converted.

The following examples, references and figures are provided to aid the understanding of the present invention, the true scope of which is set forth in the appended claims. It is understood that modifications can be made in the procedures set forth without departing from the spirit of the invention.

EXAMPLES

Example 1

1 Production of Guanidinium Hydrogen Sulfite 130 g (722 mmol) of guanidine carbonate (Fluka 50930) was dissolved in 700 ml of water at room temperature. A stream of $SO_2$ was bubbled through this solution for several hours until pH 2-3 was measured. The yellow solution was lyophilised. The yield of the colorless product was 184 g.

$^1$H-NMR ([$D_6$]DMSO, 300 MHz): δ=7.12 (s, 6H).

$^{13}$C-NMR ([$D_6$]DMSO, 75 MHz): δ=158.3.

Elementary analysis yielded data as expected.

Example 2

Figure 2:
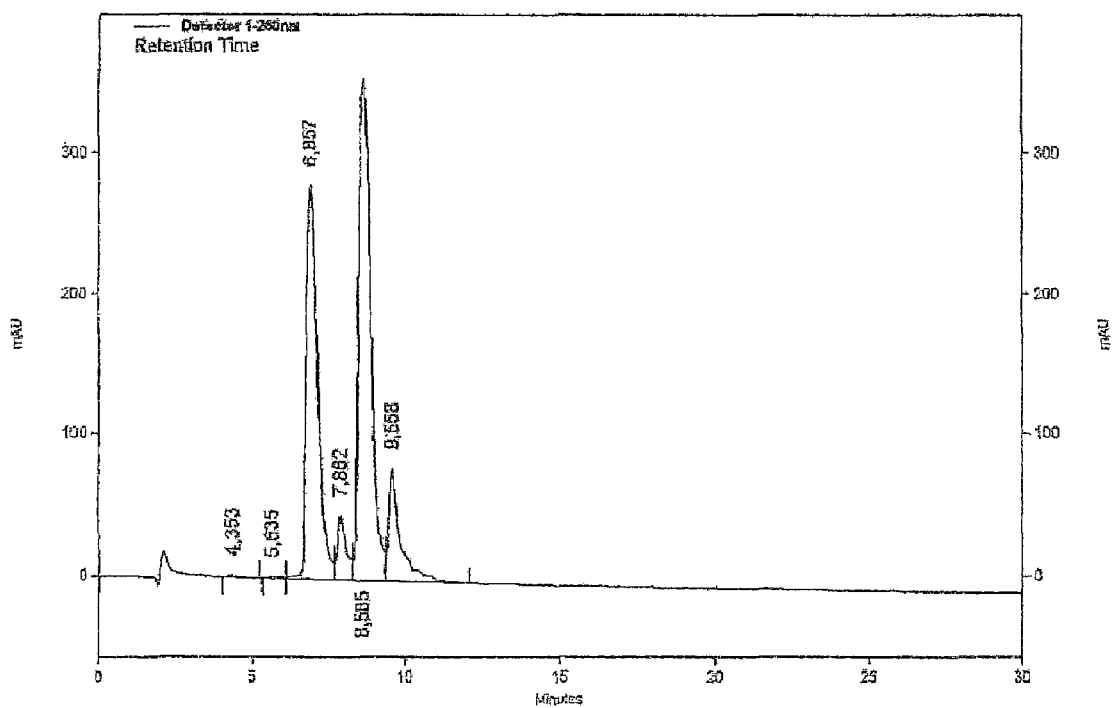
Figure 2:
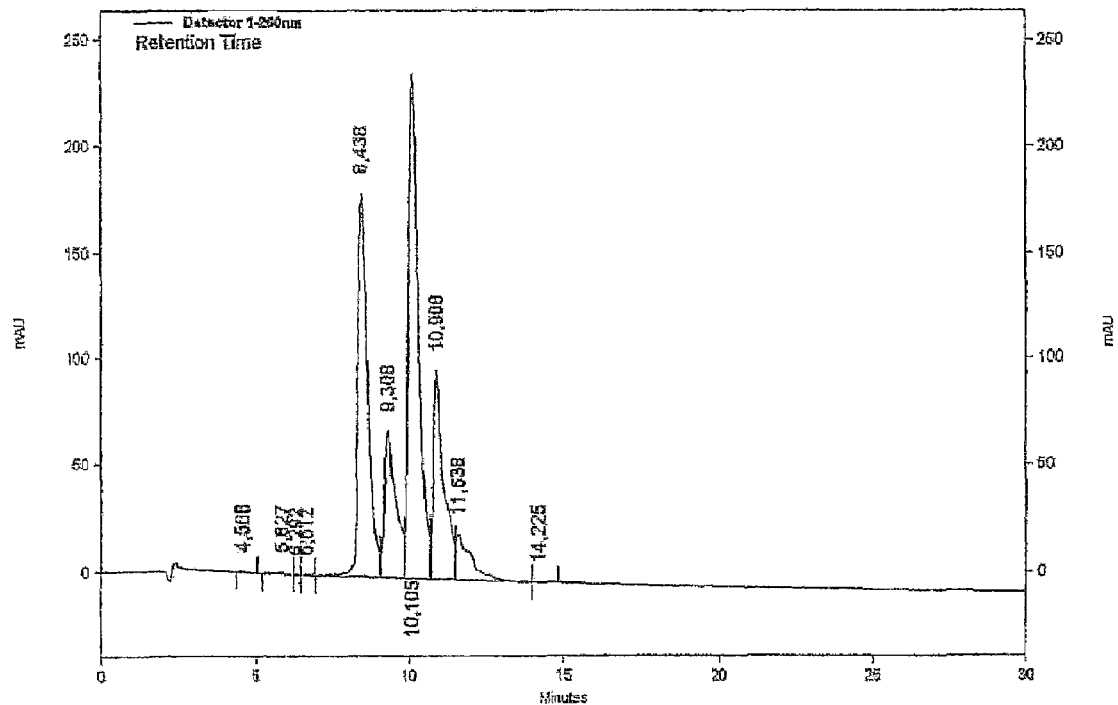
Figure 3A:
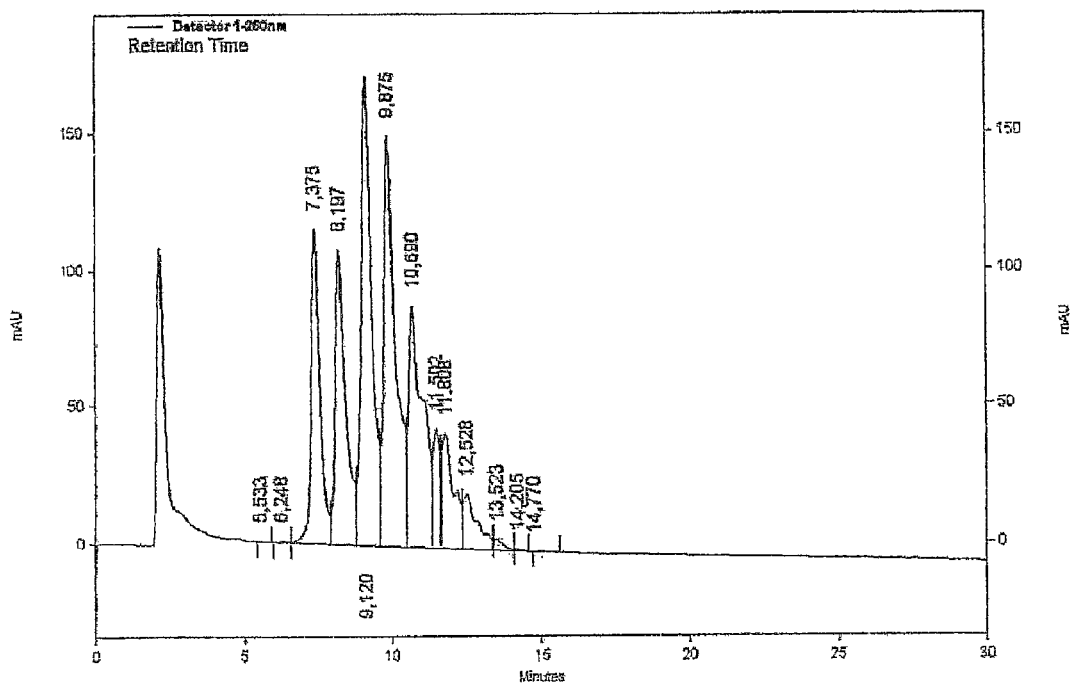
FIG. 3a) 2 M sodium hydrogensulfite, 30 min.
Figure 3:
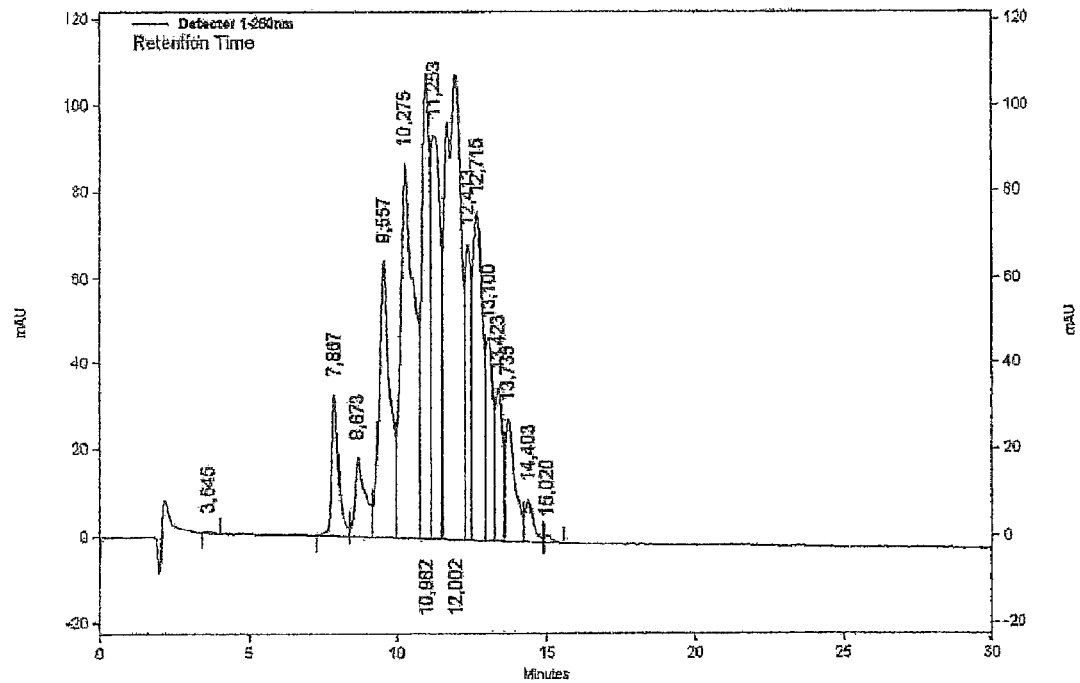
Figure 4A:
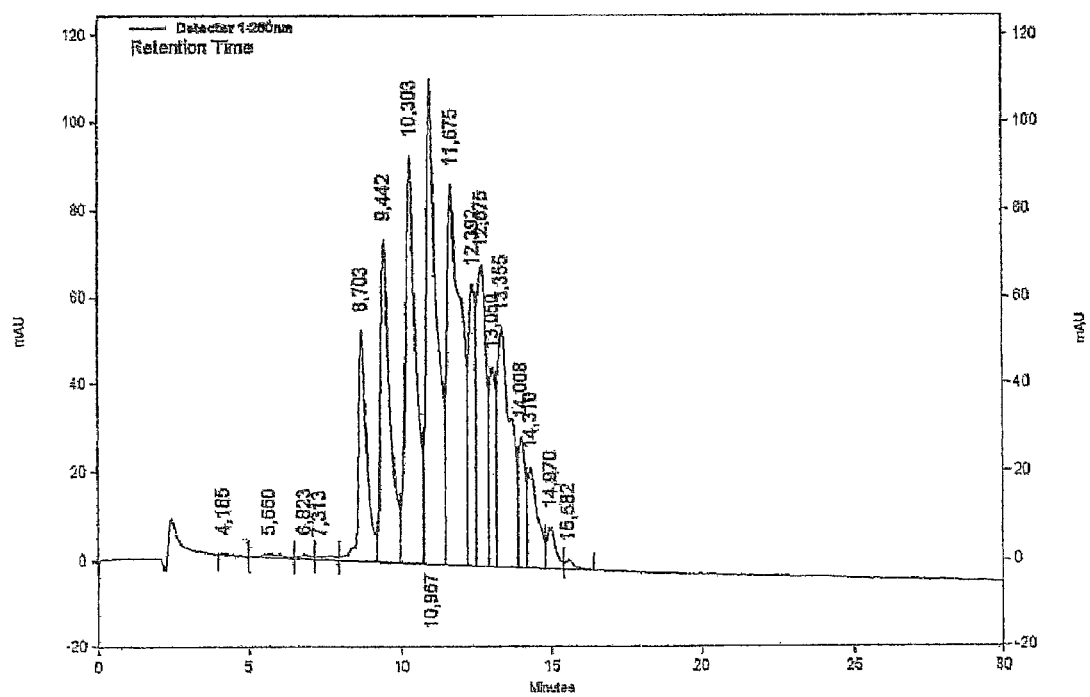
FIG. 4a) 2 M sodium hydrogensulfite, 60 min.
Figure 4B:
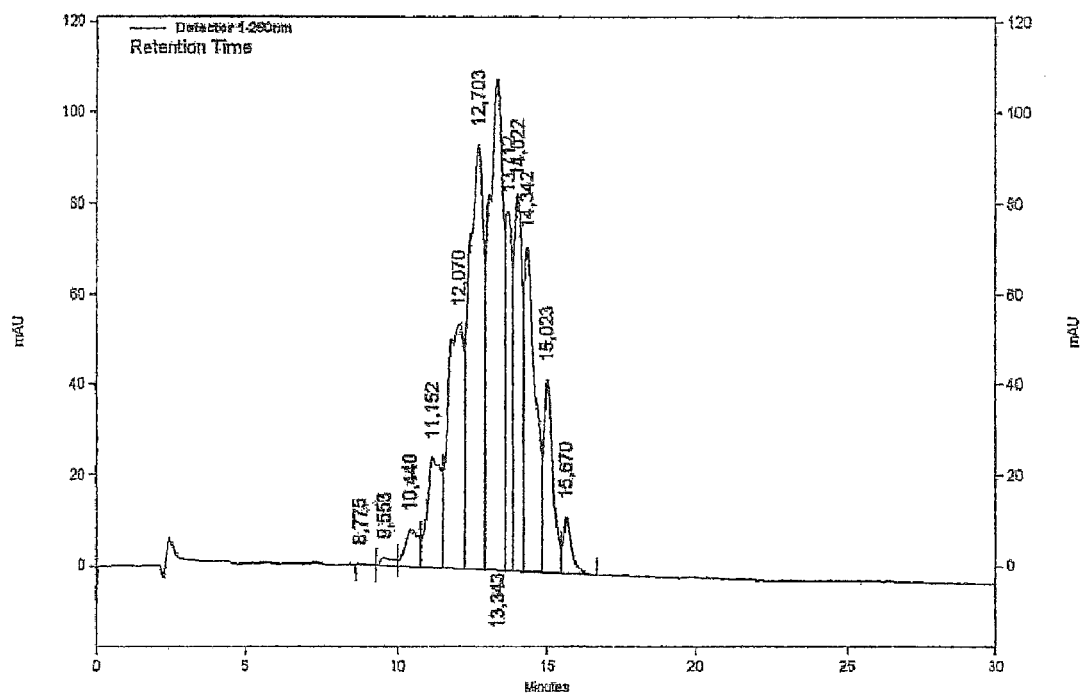
FIG. 4b) 2 M guanidinium hydrogensulfite, 60 min.

2 Desamination Reaction with an Oligonucleotide 2.1.1 Experimental Design:

A double stranded nucleic acid formed from two oligonucleotides ("GSTP1 ds") is treated with sodium disulfite or guanidinium hydrogensulfite in different molar concentrations. After this procedure the GSTP1 ds is desulfonated and desalted. The purified GSTP1 ds is analysed by HPLC (see FIGS. 2 to 4). The two oligonucleotides forming the double-stranded nucleic acid ("GSTP1 ds") are described below and have the sequences SEQ ID NO: 1 and 2.

2.1.2 Method 2.1.2.1 Oligonucleotides

```
Oligo 1:
5'-GGG ACT CCA GGG CGC CCC TC-3'    (SEQ ID NO: 1)
MW = 6079.97 Da
1 OD = 5.04 nmol Oligo 2:
5'-GAG GGG CGC CCT GGA GTC CC-3'    (SEQ ID NO: 2)
MW = 6159.99 Da
1 OD 4.83 nmol
```

2.1.2.2 Deamination of GSTP1 ds Using Sodium Disulfite:

5 nmol (MW 12239.96 Da) of GSTP1 ds are mixed with 200 µl of bisulfite reagent (1-2M, pH 5.5) and incubated for several minutes (30 min-60 min) at 80° C.

2.1.2.3 Deamination of GSTP1 ds Using Guanidinium Hydrogensulfite:

5 nmol (MW 12239.96 Da) of GSTP1 ds are mixed with 200 ul of bisulfite reagent (1-2M, pH 5.5) and incubated for several minutes (30 min-60 min) at 80° C.

2.1.2.4 Desulfonation and Desalting:

200 µl of the deaminated GSTP1 ds are mixed with 500 µl of 2N KOH and left for 30 minutes at room temperature. Thereafter a gel filtration with water on Sephadex G-25M (Pharmacia, Code No. 17-0851-01, Lot. No. QG 11018, bed volume 9 ml) takes place. The solvent is removed and the residue dissolved in 200 µl of water. 40 µl are used for the HPLC.

2.1.2.5 HPLC:

Column: Dionex DNAPac PA-100SEL, 4×250 mm with pre-column: Product No. SP3816 Serial No. 0440
Solvent A: 0.2 M NaCl in 0.01 M NaOH
Solvent B: 1 M NaCl in 0.01 M NaOH
Gradient: 0 min: 50% A/50% B
25 min: 100% B, 1 ml/min The kinetic of the bisulfite reaction is analysed via HPLC. It is shown that under the same conditions the kinetic of the deamination process is much faster with relative low concentrations (2 M) of guanidinium hydrogensulfite in comparison with the standard reagent sodiumhydrogensulfite (see FIGS. 2 to 4). This shows clearly at relative low bisulfite concentration the advantages of the chaotropic guanidinium cation over sodium. The chromatogram of the 1 M bisulfite reaction is an example of the status shortly after starting the bulfite reaction. As later the elution the more the deamination reaction is completed.

Example 3

3 Establishment of a LC-PCR Specific for Bisulphite Treated DNA

General

The fact that the bisulfite reaction has worked and converted non-methylated cytosines to uracil can be demonstrated by a polymerase chain reaction whereby primers are used which are specific to a region of the nucleic acid sequence wherein non-methylated cytosines have been converted to uracils, i.e. the base adenine in the primer is opposite to the uracil being the bisulfite reaction product from non-methylated cytosines. In case of incomplete conversion, the primer could not hybridize to this region as there would be cytosines not matching the adenine bases in the primer. This would have the effect that no PCR product would be obtained.

An improved method to perform rapid polymerase chain reactions is disclosed e.g. in U.S. Pat. No. 6,174,670 and is used in the LightCycler® instrument (Roche, Mannheim, Germany). In this method, two labeled probes can come into close proximity in an amplificate dependent manner so that the two labels can perform a fluorescence energy transfer (FRET). The amount of the amplificate thereby correlates with the intensity of the emitted light of a certain wavelength. This specific PCR method can therefore be used to analyze whether a complete conversion of non-methylated cytosines was obtained, by e.g. analyzing the promoter region of the glutathion-S-transferase π gene (see e.g. SEQ ID NO: 3 for the full length sequence of this gene and the promoter, U.S. Pat. No. 5,552,277, Genbank accession code M24485 and Morrow, C. S., et al., Gene 75 (1989) 3-11) using suitable probes and primers. However, the expert skilled in the art knows that other methods can be used for this evaluation as well. Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i = N_o \times (1+E)^i$, where $N_o$=the number of target molecules at the start of the reaction, $N_i$=the number of target molecules at the completion of the i-th cycle, E=the efficiency of the amplification (0=<E=<1). During this geometric growth phase of the amplification, the number of cycles required to reach a particular threshold value ($C_T$ value or crossing point) is inversely proportional to the logarithm of (1+E). Thus, the $C_T$ value represents a measure of the reaction efficiency that allows comparisons between reactions. A decrease in the $C_T$ value, which means that the reaction reached the threshold value in fewer cycles, indicates an increase in reaction efficiency. As the increase in amplification product is monitored by measuring the increase in reaction fluorescence, the $C_T$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value or crossing point, was calculated by interpolating fluorescence measurements between cycles.

General Methodology

The following experiment demonstrates that the described PCR on the LightCycler® instrument can be used as an evaluation tool for bisulfite treated DNA. It shows that the designed primer/probe combination gives positive results only with DNA after bisulfite treatment. Bisulfite treated DNA (in this case bisulfite DNA was treated according to the protocol described in example 2) and untreated DNA were amplified in parallel using the same template concentrations (20 ng and 1 ng per PCR). PCR analysis on the LightCycler® instrument 3.1.1 Composition of Mastermix:

LC FastStart DNA Master HybridizationProbe 1×, 2 mM MgCl2, forward Primer 0.5 µM, reversed Primer 0.5 µM, donor probe 250 nM, acceptor probe 250 nM, template 10 µl, total PCR volume 20 µl.

3.1.2 PCR-Conditions:

Denaturation 10 min/95° C.

| 55 cycles | 95° C./10 s |
| | 65° C./10 s - signal acquisition |
| | 72° C./10 s    Ramp time 20° C./s |

3.1.3 Results

| MDNA/PCR | Bisulphite treatment | $C_T$-Value or Crossingpoint |
| --- | --- | --- |
| 20 ng | Yes | 30.55 |
| | | 29.72 |
| | | 29.95 |
| | | 30.06 |
| 1 ng | yes | 34.7 |
| | | 35.8 |
| | | 34.07 |
| | | 33.86 |
| 20 ng | No | No growth curve |
| | | No growth curve |
| | | No growth curve |
| | | No growth curve |
| 1 ng | No | No growth curve |
| | | No growth curve |
| | | No growth curve |
| | | No growth curve |

The result shows crossing points only for bisulfite treated DNA. Therefore this PCR is suitable in evaluating bisulfite methods. For those skilled in the art it is clear that any PCR might be used as an evaluation tool if it is guaranteed that the primer/probe combination does not react with DNA before bisulfite treatment.

Example 4

4 Gua-Hydrogen-Sulfite can Replace the Standard Deamination Reagent Sodium-Bisulfite During Analysis of DNA Methylation Experimental Design:

Methylated DNA is spiked in unmethylated DNA, denatured and then treated in parallel with sodium bisulfite or guanidinium hydrogen sulfite. Thereafter, the DNA is desalted using magnetic glass particles, desulfonated and again desalted. The purified DNA is analysed using a real time kinetic PCR protocol that detects only bisulfite treated methylated DNA.

4.1.1 Denaturation of DNA:

100 µl of methylated DNA (Serologicals Corporation, Norcross, Ga., USA; Cat S 7821) dilution (50 ng/assay spiked in 1000 ng HDNA background, Roche Cat.1691112; 5 replicates per method), and 11 µl 2 M NaOH are mixed and incubated for 10 min at 37° C.

4.1.2 Deamination of DNA: Method 1 Using Standard Reagent Sodium-Bisulfite

111 µl of the denatured DNA are mixed with 200 µl bisulfite reagent (2.5M sodium bisulfite=5M sulfite solution, 125 mM hydroquinone, pH 5.5) and incubated for 2 h at 80° C.

4.1.3 Deamination of DNA: Method 2 Using Reagent Guanidinium-Hydrogen-Sulfite

111 µl of the denatured DNA are mixed with 200 µl bisulfite reagent (5M guanidinium hydrogen sulfite, pH 5.5) and incubated for 2 h at 80° C.

4.1.4 Processing Using MGPs

311 µl of the deaminated DNA are mixed with 600 µl binding buffer (MagNAPure DNA Isolation Kit I, Roche Cat. Nr. 3 003 990) and 75 µl magnetic glass particle solution (MagNAPure DNA Isolation Kit I) and incubated for 15 min/room temperature with continuous mixing. Thereafter, the magnetic glass particles are washed three times with 1 ml 70% Ethanol. Bound free separation is done in a magnetic separator (Roche Cat.1641794). Thereafter, desulphonation takes place by adding 250 µl 90% EtOH/20 mM NaOH to the DNA bound to the MGPs; the mixture is incubated for 10 min at room temperature with mixing. Thereafter the MGPs are washed two times with 90% Ethanol. To remove ethanol rests the MGPs are heated for 15 min./60° C. in a thermomixer with open lid. Thereafter the DNA is eluted with 50 µl 10 mM Tris/0.1 mM EDTA pH 7.5 (15 min/60° C.). 10 µl of the eluted DNA is used for subsequent PCR analysis.

Analysis of Deaminated DNA on the LightCyler® Instrument 4.1.5 Composition of Mastermix LightCycler® FastStart DNA Master HybridizationProbe 1× (Roche 2239272), 3 mM MgCl2, forward Primer 0.4 µM, reversed Primer 0.4 µM, donor probe 200 nM, acceptor probe 200 nM, template 10 µl, total PCR volume 20 µl.

4.1.6 PCR-Conditions

Denaturation 10 min/95° C.

| 55 cycles | 95° C./10 s |
| | 62° C./10 s - signal acquisition |
| | 72° C./10 s    Ramp time 20° C./s |

Results:

| replicates | Methylated DNA/PCR | Sodium bisulfite reagent $C_T$-Values or Crossing points | Guanidinium hydrogensulfite reagent |
| --- | --- | --- | --- |
| 1 | 10 ng | 30.24 | 29.22 |
| 2 | 10 ng | 29.68 | 29.85 |
| 3 | 10 ng | 30.20 | 29.64 |
| 4 | 10 ng | 29.89 | 29.74 |
| 5 | 10 ng | 29.81 | 29.18 |
| Mean value | | 29.96 | 29.53 |

The $C_T$-values or crossing points calculated during real time PCR are almost identical for both sulfite reagents used, for guanidinium hydrogensulfite the mean value is even lower; i.e. that guanidinium hydrogensulfite can replace the standard deamination reagent showing a somewhat better performance.

Example 5

5 Use of Guanidinium Hydrogen Sulfite Without Prior Denaturation of DNA for Methylation Analysis Experimental Design:

Methylated DNA is spiked in unmethylated DNA, denatured or not denatured and then treated in parallel with sodium bisulfite or guanidinium hydrogen sulfite. Thereafter, the DNA is desalted using magnetic glass particles, desulfonated and again desalted. The purified DNA is analysed using a real time kinetic PCR protocol that detects only bisulfite treated methylated DNA.

5.1.1 Denaturation of DNA:

100 μl of methylated DNA (Serologicals Corporation, Norcross, Ga., USA; Cat S 7821) dilution (50 ng/assay spiked in 1000 ng hDNA background, Roche Cat.1691112; 4 replicates per method), and 11 μl 2 M NaOH are mixed and incubated for 10 min at 37° C.

5.1.2 Deamination of DNA: Method 1 Using Standard Reagent Sodium-Bisulfite

111 μl of the denatured DNA or 100 μl of not denatured DNA are mixed with 200 μl bisulfite reagent (2.5M sodium bisulfite, 125 mM hydroquinone, pH 5.5) and incubated for 2 h at 80° C.

10 mM Tris/0.1 mM EDTA pH 7.5 (15 min./60° C.). 10 μl of the eluted DNA is used for subsequent PCR analysis.

Analysis of Deaminated Treated DNA on the LightCycler® Instrument 5.1.5 Composition of Mastermix LightCycler® FastStart DNA Master HybridizationProbe 1× (Roche 2239272), 3 mM MgCl2, forward Primer 0.4 μM, reversed Primer 0.4 μM, donor probe 200 nM, acceptor probe 200 nM, template 10 μl, total PCR volume 20 μl.

5.1.6 PCR-Conditions

Denaturation 10 min/95° C.

| 55 cycles | 95° C./10 s |  |
|---|---|---|
|  | 62° C./10 s - signal acquisition |  |
|  | 72° C./10 s | Ramp time 20° C./s |

Results:

| replicates | Methylated DNA/PCR | Sodium disulfite reagent with denaturation | Guanidinium hydrogensulfite reagent with denaturation | Sodium disulfite reagent without denaturation | Guanidinium hydrogensulfite reagent without denaturation |
|---|---|---|---|---|---|
|  |  | $C_T$-Values or Crossing points |  |  |  |
| 1 | 10 ng | 29.74 | 29.06 | 34.35 | 33.62 |
| 2 | 10 ng | 29.48 | 29.85 | 35.17 | 33.92 |
| 3 | 10 ng | 29.66 | 29.86 | 33.64 | 33.60 |
| 4 | 10 ng | 29.80 | 29.86 | 33.10 | 33.63 |
| Mean value |  | 29.67 | 29.66 | 34.07 | 33.69 |

5.1.3 Deamination of DNA: Method 2 Using Reagent Guanidinium-Hydrogen-Sulfite

111 μl of the denatured DNA or 100 μl of not denatured DNA are mixed with 200 μl bisulfite reagent (5M guanidinium hydrogen sulfite, pH 5.5) and incubated for 2 h at 80° C.

5.1.4 Processing Using MGPs

311 μl of the deaminated DNA are mixed with 600 μl binding buffer (MagNAPure DNA Isolation Kit I, Roche Cat. Nr. 3 003 990) and 75 μl magnetic glass particle solution (MagNAPure DNA Isolation Kit I) and incubated for 15 min/room temperature with continuous mixing. Thereafter, the magnetic glass particles are washed three times with 1 ml 70% Ethanol. Bound free separation is done in a magnetic separator (Roche Cat.1641794). Thereafter, desulphonation takes place by adding 250 μl 90% EtOH/20 mM NaOH to the DNA bound to the MGPs; the mixture is incubated for 10 min at room temperature with mixing. Thereafter the MGPs are washed two times with 90% Ethanol. To remove residual ethanol the MGPs are heated for 15 min/60° C. in a thermomixer with open lid. Thereafter the DNA is eluted with 50 μl The result shows that the Bisulfite reaction does work without prior denaturation of DNA; the novel reagent guanidinium hydrogen sulfite is more efficient because the median of the crossing points is lower than that of the standard bisulfite reagent.

Example 6

6 Guanidinium Hydrogensulfit can be Used in Lower Molar Concentrations for Methylation Analysis Experimental Design:

Methylated DNA is spiked in unmethylated DNA, denatured and then treated in parallel with sodium disulfite or guanidinium hydrogen sulfite in different molar concentrations. Thereafter, the DNA is desalted using magnetic glass particles, desulfonated and again desalted. The purified DNA is analysed using a real time kinetic PCR protocol that detects only bisulfite treated methylated DNA.

6.1.1 Denaturation of DNA:

100 μl of methylated DNA (Serologicals Corporation, Norcross, Ga., USA; Cat S 7821) dilution (50 ng/assay spiked in 1000 ng HDNA background, Roche Cat.1691112; 4 replicates per method), and 11 µl 2 M NaOH are mixed and incubated for 10 min at 37° C.

6.1.2 Deamination of DNA: Method 1 Using Standard Reagent Sodium-Bisulfite

111 µl of the denatured DNA or 100 µl of not denatured DNA are mixed with 200 µl bisulfite reagent (2.5M-1.5M-0.5M sodium disulfite, 125 mM hydroquinone, pH 5.5) and incubated for 2 h at 80° C. (Comment: a 2.5M solution of sodium disulfite is 5M regarding sulfite ions)

6.1.3 Deamination of DNA: Method 2 Using Reagent Guanidinium-Hydrogen-Sulfite

111 µl of the denatured DNA or 100 µl of not denatured DNA are mixed with 200 µl bisulfite reagent (5M-3M-1M guanidinium hydrogen sulfite, pH 5.5) and incubated for 2 h at 80° C.

6.1.4 Processing Using MGPs

311 µl of the deaminated DNA are mixed with 600 µl binding buffer (MagNAPure DNA Isolation Kit I, Roche Cat. Nr. 3 003 990) and 75 µl magnetic glass particle solution (MagNAPure DNA Isolation Kit I) and incubated for 15 min/room temperature with continuous mixing. Thereafter, the magnetic glass particles are washed three times with 1 ml 70% Ethanol. Bound free separation is done in a magnetic separator (Roche Cat.1641794). Thereafter, desulphonation takes place by adding 250 µl 90% EtOH/20 mM NaOH to the DNA bound to the MGPs; the mixture is incubated for 10 min at room temperature with mixing. Thereafter the MGPs are washed two times with 90% Ethanol. To get rid of ethanol rests the MGPs were heated for 15 min./60° C. in a thermomixer with open lid. Thereafter the DNA is eluted with 50 µl 10 mM Tris/0.1 mM EDTA pH 7.5 (15 min./60° C.). 10 µl of eluted DNA is used for subsequent PCR analysis.

Analysis of Deaminated Treated DNA on the Lightycler® Instrument 6.1.5 Composition of Mastermix LightCycler® FastStart DNA Master HybridizationProbe 1× (Roche 2239272), 3 mM MgCl2, forward Primer 0.4 µM, reversed Primer 0.4 µM, donor probe 200 nM, acceptor probe 200 nM, template 10 µl, total PCR volume 20 µl.

6.1.6 PCR-Conditions

Denaturation 10 min/95° C.

| 55 cycles | 95° C./10 s |
| | 62° C./10 s - signal acquisition |
| | 72° C./10 s    Ramp time 20° C./s |

Results:

| Replicates | Methylated DNA/PCR | Amount of sulfite during deamination reaction | Sodium disulfite reagent $C_T$-Values or Crossing points | Guanidinium hydrogensulfite reagent $C_T$-Values or Crossing points |
|---|---|---|---|---|
| 1 | 10 ng | 5 M | 29.24 | 28.56 |
| 2 | 10 ng | 5 M | 29.36 | 29.35 |
| 3 | 10 ng | 5 M | 29.19 | 28.87 |
| 4 | 10 ng | 5 M | 29.61 | 28.94 |
| Mean value | | | 29.35 | 28.93 |
| 1 | 10 ng | 3 M | 30.67 | 29.76 |
| 2 | 10 ng | 3 M | 30.20 | 29.68 |
| 3 | 10 ng | 3 M | 30.61 | 30.59 |
| | 10 ng | 3 M | 31.10 | 30.53 |
| Mean value | | | 30.65 | 30.14 |
| 1 | 10 ng | 1 M | — | — |
| 2 | 10 ng | 1 M | — | — |
| 3 | 10 ng | 1 M | — | — |
| 4 | 10 ng | 1 M | 41.64 | — |
| Mean value | | | | |

The results show that desamination is also possible with a lower molar concentration of sulfite ions, but the sensitivity drops; a concentration of 1M is too low. The novel reagent is somewhat more efficient because the difference in crossing points between 5M and 3M is 1.21, whereas for the standard reagent it is 1.3.

Example 7

7 GuaSulfit can be Used for Solid Phase Deamination in DNA Methylation analysis

Experimental Design

Methylated DNA is spiked in unemthylated DNA, denatured in solution and transfer to silica solid phase (column). Deamination is done in parallel with sodium disulfite or guanidinium hydrogen sulfite. Thereafter the DNA is desalted, desulfonated and again desalted. The purified DNA is analysed using a real time kinetic PCR protocol that detects only bisulfite treated methylated DNA.

7.1.1 Denaturation of DNA:

100 µl of methylated DNA (Serologicals Corporation, Norcross, Ga., USA; Cat S 7821) dilution (50 ng/assay spiked in 1000 ng HDNA background, Roche Cat.1691112; 3 replicates per method), and 11 µl 2 M NaOH are mixed and incubated for 15 min at 37° C.

7.1.2 Solid Phase Deamination of DNA: Method 1 Using Standard Reagent Sodium-Bisulfite 111 µl of the denatured DNA are mixed with 300 µl bisulfite reagent (2.5M sodium bisulfite=5M sulfite in solution, pH 5.5) and 100 µl ethanol and loaded on to a silica column (from High Pure Template Preparation Kit, Roche, 1796828); incubation is overnight at 50° C.

7.1.3 Solid Phase Deamination of DNA: Method 2 Using Reagent Guanidinium-Hydrogen-Sulfite 111 µl of the denatured DNA are mixed with 300 µl bisulfite reagent (5M guanidinium hydrogensulfite, pH 5.5) and 100 µl ethanol and loaded on to a silica column (from High Pure Template Preparation Kit, Roche, 1796828); incubation is overnight at 50° C.

7.1.4 Processing on Silica Columns

After overnight incubation columns are centrifuged 1 min/8000 rpm (Eppendorf bench top centrifuge) and two times washed with 500 µl 70% ethanol. Desulfonation is performed by adding 500 µl reagent (38% ethanol/100 mM EDTA/200 mM NaOH) and incubation for 20 min. at room temperature. After short centrifugation the columns are washed twice with 500 µl 90% ethanol each. To remove the entire ethanol the columns are centrifuged for 20 sec at 14000 rpm. Bound DNA is eluted by adding 100 μl prewarmed (70° C.) PCR grade water. The columns are centrifuged again and the supernatant is used for subsequent PCR analysis Analysis of Deaminated Treated DNA on the LightCycler® Instrument 7.1.5 Composition of Mastermix LightCycler® FastStart DNA Master HybridizationProbe 1× (Roche 2239272), 3 mM MgCl2, forward Primer 0.4 μM, reversed Primer 0.4 μM, donor probe 200 nM, acceptor probe 200 nM, template 10 μl, total PCR volume 20 μl.

7.1.6 PCR-Conditions

Denaturation 10 min/95° C.

| 55 cycles | 95° C./10 s |
| | 62° C./10 s - signal acquisition |
| | 72° C./10 s    Ramp time 20° C./s |

Results:

| Replicates | Solid phase desamination with Sodium disulfite reagent | Solid phase desamination with Guanidinium hydrogensulfite reagent |
|---|---|---|
| | $C_T$-Values or Crossing points | |
| 1 | 32.72 | 31.68 |
| 2 | 32.85 | 31.64 |
| 3 | 32.47 | 31.75 |
| Mean value | 32.68 | 31.69 |

The results show that solid phase desamination is possible with both sulfite reagents, but the efficiency for the novel reagent is significantly higher: the resulting crossing points are 1 cycle earlier corresponding to a twofold better yield of bisulfite treated DNA.

Example 8

8 GuaSulfit can be Used for Combined Process SP+BIS

Experimental Design

A clinical sample is directly contacted with the bisulfite reagent (GuaSulfit or Na-Bisulfit) without prior purification of the DNA. After incubation the processing of the converted DNA is done using the magnetic glass particles as usual. The purified DNA is analysed using a real time kinetic PCR protocol that detects only bisulfite treated DNA.

8.1.1 Combined SP and BIS Process:

200 μl of normal human serum or normal human serum spiked with 0.2 μg of nucleosomal DNA (3 replicates each) are mixed with 50 μl Proteinase K (Roche) and 600 μl BIS reagent (either 6M Guanidiniumhydrogen-Sulfit or 5M Sodiumbisulfite); pH is adjusted to 5.5 with 5M NaOH. Then the mixture is incubated for 2 h at 80° C. in a thermomixer.

8.1.2 Processing Using MGPs

Thereafter 6 mg magnetic glass particles ((MagNAPure DNA Isolation Kit I, Roche Cat. Nr. 3 003 990) in 600 μl isopropanol are added, and the solution is mixed thoroughly and incubated for 15 min/room temperature with continuous mixing. Thereafter, the magnetic glass particles are washed three times with 1 ml 70% Ethanol. Bound free separation is done in a magnetic separator (Roche Cat. 1641794). Thereafter, desulphonation takes place by adding 250 μl 90% EtOH/20 mM NaOH to the DNA bound to the MGPs; the mixture is incubated for 10 min at room temperature with mixing. Thereafter the MGPs are washed two times with 90% Ethanol. To get rid of ethanol rests the MGPs were heated for 15 min./60° C. in a thermomixer with open lid. Thereafter the DNA is eluted with 500 μl 10 mM Tris/0.1 mM EDTA pH 7.5 (15 min./60° C.). 10 μl of the eluted DNA is used for subsequent PCR analysis.

Analysis of Deaminated Treated DNA on the LightCycler® Instrument 8.1.3 Composition of Mastermix LightCycler® FastStart DNA Master HybridizationProbe 1× (Roche 2239272), 2 mM MgCl2, forward Primer 0.5 μM, reversed Primer 0.5 μM, donor probe 300 nM, acceptor probe 300 nM, template 10 μl, total PCR volume 20 μl.

8.1.4 PCR-Conditions

Denaturation 10 min/95° C.

| 55 cycles | 95° C./10 s |
| | 62° C./10 s - signal acquisition |
| | 72° C./10 s    Ramp time 20° C./s |

Results:

| Sample | Sodium disulfite reagent | Guanidinium hydrogensulfite reagent |
|---|---|---|
| | $C_T$-Values or Crossing points | |
| NS | No growth curve | 43.04 |
| NS | No growth curve | 37.67 |
| NS | No growth curve | 40.96 |
| Mean value | — | 40.56 |
| NS + DNA | 36.75 | 35.37 |
| NS + DNA | 37.56 | 34.40 |
| NS + DNA | 37.55 | 36.26 |
| Mean value | 37.29 | 35.34 |

The results show that the new format "combination of Sample preparation and BIS-Treatment" results in converted, amplifiable DNA. For the standard BIS reagent positive results are seen only for the spiked samples; that means that the overall efficiency of the process is still quite limited. In contrast however using the novel BIS reagent results in positive results for the unspiked serum as well as the spiked serum, indicating that the novel BIS reagent can be used more efficiently for the combined SP-BIS format than the standard reagent.

Example 9

9 GuaSulfit can be Used as Binding Reagent for DNA Isolation on Silica Surfaces

Experimental Design 50 ng human genomic DNA, Roche 1691112 is spiked in 200 μl normal negative serum. Then the DNA is isolated using the High Pure Template preparation kit (Roche 1796828) either with the recommended binding buffer or with 5M Guanidinium hydrogensulfit pH 5.5 or 5M Sodium Bisulfite pH 5.5 as binding buffer (3 replicates each). The purified DNA is then quantified in a real time kinetic PCR using the LC Control Kit (Roche 2015102) that detects β Globin DNA.

Results

| Replicates | Original Binding Buffer | | 5 M Sodium Bisulfite as Binding buffer | | 5 M Guanidinium Hydrogensulfite as Binding buffer | |
|---|---|---|---|---|---|---|
| | cp | ng DNA | cp | ng DNA | cp | ng DNA |
| 1 | 26.6 | 50.2 | 28.97 | 9.56 | 29.61 | 6.11 |
| 2 | 26.59 | 50.4 | 28.72 | 11.4 | 29.36 | 7.32 |
| 3 | 26.74 | 45.6 | 28.95 | 9.74 | 29.56 | 6.34 |
| Mean value | 26.64 | 48.7 | 28.88 | 10.2 | 29.51 | 6.6 |

The results show that the original binding buffer in the kit gives the best performance, but both sulfite reagents might be used also as binding buffers; the novel reagent is somewhat less efficient and some more optimization might be needed.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited is this application are incorporated by reference in their entirety for all purposes to the same extent as if each individual publication, patent, patent application, and/or other document were individually indicated to be incorporated by reference of all purposes.

The invention claimed is:

1. A method for the conversion of a cytosine base, in a nucleic acid to an uracil base comprising:
   a) providing a solution that contains a nucleic acid,
   b) providing guanidinium hydrogen sulfite and preparing a solution consisting of aqueous solvent, guanidinum and sulfite ions,
   c) mixing the solutions from step a) and b),
   d) incubating the solution obtained in step c) containing the nucleic acid and guanidinium and sulfite ions whereby the nucleic acid is deaminated,
   e) incubating the deaminated nucleic acid under alkaline conditions whereby the deaminated nucleic acid is desulfonated, and
   f) isolating the deaminated nucleic acid.

2. The method according to claim 1, wherein the concentration of guanidinium ions and sulfite ions is between 0.1 and 8 M.

3. The method according to claim 1, wherein the pH of the solutions in step b) and c) is less than 7.0.

4. The method according to claim 1, characterized in that the temperature of said incubation in step d) and e) is between 0° C. and 90° C.

5. The method according to claim 1, wherein the time of said incubation in step d) is between 30 min and 48 hours.

6. The method according to claim 1, wherein step e) is performed by adding an alkaline solution or buffer, or a solution containing ethanol, sodium chloride and sodium hydroxide.

7. The method according to claim 1, wherein the temperature of said incubation in step e) is between 0° C. and 90° C.

8. The method according to claim 1, wherein the time of said incubation in step e) is between 5 min and 60 min.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Homo sapiens

<400> SEQUENCE: 1
gggactccag ggcgccctc                                               20

<210> SEQ ID NO 2
<211> LENGTH: 20
<212> TYPE: DNA
<213> ORGANISM: Homo sapiens

<400> SEQUENCE: 2 gagggcgcc ctggagtccc                                               20

<210> SEQ ID NO 3
<211> LENGTH: 4261
<212> TYPE: DNA
<213> ORGANISM: Homo sapiens
<220> FEATURE:
<221> NAME/KEY: misc_signal
<222> LOCATION: (1156)..(1162)
<223> OTHER INFORMATION: transcription regulatory motif; putative
<220> FEATURE:
<221> NAME/KEY: GC_signal
<222> LOCATION: (1169)..(1174)
<220> FEATURE:
<221> NAME/KEY: GC_signal
<222> LOCATION: (1179)..(1184)
<220> FEATURE:
<221> NAME/KEY: GC_signal
<222> LOCATION: (1194)..(1198)
<220> FEATURE:
<221> NAME/KEY: GC_signal
<222> LOCATION: (1225)..(1254)
<220> FEATURE:
<221> NAME/KEY: GC_signal
<222> LOCATION: (4041)..(4046)
<300> PUBLICATION INFORMATION:
<301> AUTHORS: Morrow et al.
<302> TITLE: Structure of the human genomic glutathion S-transferase pi
      gene
<303> JOURNAL: Genes and Development
<304> VOLUME: 75
<306> PAGES: 3-11
<307> DATE: 1989-01-01
<300> PUBLICATION INFORMATION:
```

<308> DATABASE ACCESSION NUMBER: M24485
<309> DATABASE ENTRY DATE: 2000-03-04
<313> RELEVANT RESIDUES: (1)..(4261)
<300> PUBLICATION INFORMATION:
<302> TITLE: Genetic Diagnosis of Prostate cancer
<310> PATENT DOCUMENT NUMBER: US5,552,277
<311> PATENT FILING DATE: 1994-07-19
<312> PUBLICATION DATE: 1996-09-03
<313> RELEVANT RESIDUES: (1)..(4261)

<400> SEQUENCE: 3

```
aacaagagat caatatctag aataaatgga gatctgcaaa tcaacagaaa gtaggcagca      60
aagccaaaga aaatagccta aggcacagcc actaaaagga acgtgatcat gtcctttgca     120
gggacatggg tggagctgga agccgttagc ctcagcaaac tcacacagga acagaaaacc     180
agcgagaccg catggtctca cttataagtg ggagctgaac aatgagaaca catggtcaca     240
tggcggcgat caacacacac tggtgcctgt tgagcggggt gctggggagg gagagtacca     300
ggaagaatag ctaagggata ctgggcttaa tacctgggtg atgggatgat ctgtacagca     360
aaccatcatg gcgcacacac ctatgtaaca aacctgcaca tcctgcacat gtacccagaa     420
acttcaaata aaagttggac ggccaggcgt ggtggctcac gcctgtaatc ccagcacttt     480
gggaagccga ggcgtgcaga tcacctaagg tcaggagttc gagaccagcc cggccaacat     540
ggtgaaaccc cgtctctact aaaaatacaa aaatcagcca gatgtggcac gcacctataa     600
ttccacctac tcgggaggct gaagcagaat tgcttgaacc cgagaggcgg aggttgcagt     660
gagccgccga gatcgcgcca ctgcactcca gcctgggcca cagcgtgaga ctacgtcata     720
aaataaaata aaataacaca aaataaaata aaataaaata aaataaaata aaataataaa     780
ataaaataaa ataaaataaa ataaaataaa ataaagcaat ttccttcct ctaagcggcc      840
tccacccctc tccctgccc tgtgaagcgg gtgtgcaagc tcgggatcg cagcggtctt       900
agggaatttc cccccgcgat gtcccggcgc gccagttcgc tgcgcacact tcgctgcggt     960
cctcttcctg ctgtctgttt actccctagg ccccgctggg gacctgggaa agagggaaag   1020
gcttccccgg ccagctgcgc ggcgactccg gggactccag ggcgcccctc tgcggccgac   1080
gcccggggtg cagcggccgc cggggctggg gccggcggga gtccgcggga ccctccagaa   1140
gagcggccgg cgccgtgact cagcactggg gcggagcggg gcgggaccac ccttataagg   1200
ctcggaggcc gcgaggcctt cgctggagtt tcgccgccgc agtcttcgcc accagtgagt   1260
acgcgcggcc cgctccccgg ggatggggct cagagctccc agcatggggc caacccgcag   1320
catcaggccc gggctcccgg cagggctcct cgccacctc gagacccggg acgggggcct    1380
agggaccca ggacgtcccc agtgccgtta gcggctttca ggggccggg agcgcctcgg     1440
ggagggatgg gaccccgggg cggggaggg ggggcaggct gcgctcaccg cgccttggca     1500
tcctcccccg ggctccagca aactttcctt tgttcgctgc agtgccgccc tacaccgtgg   1560
tctatttccc agttcgaggt aggagcatgt gtctggcagg gaaggaggc aggggctggg    1620
gctgcagccc acagccctc gcccacccgg agagatccga accccttat ccctccgtcg     1680
tgtggctttt accccgggcc tccttcctgt tcccgcctc tcccgccatg cctgctcccc   1740
gccccagtgt tgtgtgaaat cttcggagga acctgtttac ctgttccctc cctgcactcc   1800
tgacccctcc ccgggttgct gcgaggcgga gtcggcccgg tccccacatc tcgtacttct   1860
ccctccccgc aggccgctgc gcggccctgc gcatgctgct ggcagatcag ggccagagct   1920
ggaaggagga ggtggtgacc gtggagacgt ggcaggaggg ctcactcaaa gcctcctgcg   1980
taagtgacca tgcccgggca aggggagggg gtgctgggcc ttagggggct gtgactagga   2040
```

-continued

```
tcggggggacg cccaagctca gtgcccctcc ctgagccatg cctcccccaa cagctatacg    2100
ggcagctccc caagttccag gacggagacc tcaccctgta ccagtccaat accatcctgc    2160
gtcacctggg ccgcacccct tggtgagtctt gaacctccaa gtccagggca ggcatgggca    2220
agcctctgcc cccggagccc ttttgtttaa atcagctgcc ccgcagccct ctggagtgga    2280
ggaaactgag acccactgag gttacgtagt ttgcccaagg tcaagcctgg gtgcctgcaa    2340
tccttgccct gtgccaggct gcctcccagg tgtcaggtga gctctgagca cctgctgtgt    2400
ggcagtctct catccttcca cgcacatcct cttcccctcc tcccaggctg gggctcacag    2460 acagcccct ggttggccca tccccagtga ctgtgtgttg atcaggcgcc cagtcacgcg    2520
gcctgctccc ctccacccaa ccccagggct ctatgggaag gaccagcagg aggcagccct    2580
ggtggacatg gtgaatgacg gcgtggagga cctccgctgc aaatacatct ccctcatcta    2640
caccaactat gtgagcatct gcaccagggt tgggcactgg gggctgaaca agaaaagggg    2700
cttcttgtgc cctcacccc cttacccctc aggtggcttg ggctgacccc ttcttgggtc    2760
agggtgcagg ggctgggtca gctctgggcc aggggcccag gggcctggga caagacacaa    2820
cctgcaccct tattgcctgg gacatcaacc agccaagtaa cgggtcatgg gggcgagtgc    2880
aaggacagag acctccagca actggtggtt tctgatctcc tggggtggcg agggcttcct    2940
ggagtagcca gaggtggagg aggatttgtc gccagtttct ggatggaggt gctggcactt    3000
ttagctgagg aaaatatgca gacacagagc acatttgggg acctgggacc agttcagcag    3060
aggcagcgtg tgtgcgcgtg cgtgtgcgtg tgtgtgcgtg tgtgtgtgta cgcttgcatt    3120
tgtgtcgggt gggtaaggag atagagatgg gcgggcagta ggcccaggtc ccgaaggcct    3180
tgaacccact ggtttggagt ctcctaaggg caatgggggc cattgagaag tctgaacagg    3240
gctgtgtctg aatgtgaggt ctagaaggat cctccagaga agccagctct aaagcttttg    3300
caatcatctg gtgagagaac ccagcaagga tggacaggca gaatgaaata gagatgagtt    3360
ggcagctgaa gtggacagga tttggtacta gcctggttgt ggggagcaag cagaggagaa    3420
tctgggactc tggtgtctgg cctggggcag acggggggt ctcaggggct gggagggatg    3480
agagtaggat gatacatggt ggtgtctggc aggaggcggg caaggatgac tatgtgaagg    3540
cactgcccgg gcaactgaag ccttttgaga ccctgctgtc ccagaaccag ggaggcaaga    3600
ccttcattgt gggagaccag gtgagcatct ggccccatgc tgttccttcc tcgccaccct    3660
ctgcttccag atggacacag gtgtgagcca tttgtttagc aaagcagagc agacctaggg    3720
gatgggctta ggccctctgc ccccaattcc tccagcctgc tcccgctggc tgagtcccta    3780 gccccctgc cctgcagatc tccttcgctg actacaacct gctggacttg ctgctgatcc    3840
atgaggtcct agcccctggc tgcctggatg cgttccccct gctctcagca tatgtggggc    3900
gcctcagtgc ccgcccaag ctcaaggcct tcctggcctc cctgagtac gtgaacctcc    3960 ccatcaatgg caacgggaaa cagtgagggt tgggggact ctgagcggga ggcagagttt    4020 gccttcctt ctccaggacc aataaaattt ctaagagagc tactatgagc actgtgttc    4080 ctgggacggg gcttaggggt tctcagcctc gaggtcggtg ggagggcaga gcagaggact    4140
agaaaacagc tcctccagca cagtcagtgg cttcctggag ccctcagcct ggctgtgttt    4200
actgaacctc acaaactaga agaggaagaa aaaaaagag agagagaaac aaagagaaat    4260
a                                                                    4261
```